United States Patent
Tanaka et al.

(10) Patent No.: US 8,792,616 B2
(45) Date of Patent: Jul. 29, 2014

(54) X-RAY IMAGE DIAGNOSIS APPARATUS AND X-RAY IMAGE PROCESSING METHOD

(75) Inventors: Manabu Tanaka, Nasushiobara (JP); Jun Sakakibara, Otawara (JP); Makoto Kaneko, Otawara (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 678 days.

(21) Appl. No.: 13/030,518

(22) Filed: Feb. 18, 2011

(65) Prior Publication Data

US 2011/0206183 A1 Aug. 25, 2011

(30) Foreign Application Priority Data

Feb. 23, 2010 (JP) .................................. 2010-037300

(51) Int. Cl.
*H05G 1/46* (2006.01)
*H05G 1/60* (2006.01)
*H05G 1/62* (2006.01)
*G01N 23/14* (2006.01)
*A61B 6/04* (2006.01)

(52) U.S. Cl.
USPC ...... 378/95; 378/8; 378/20; 378/98; 378/205; 378/209

(58) Field of Classification Search
USPC .......... 378/4, 8, 11, 20, 91, 95, 98, 98.8, 145, 378/146, 162, 163, 201, 204, 208–210, 378/901; 382/128, 131, 192, 193, 236, 325
See application file for complete search history.

(56) References Cited

U.S. PATENT DOCUMENTS

| | | |
|---|---|---|
| 5,386,450 A | 1/1995 | Ozawa |
| 5,450,464 A | 9/1995 | Sakakibara |

(Continued)

FOREIGN PATENT DOCUMENTS

| | | |
|---|---|---|
| DE | 10 2004 059 663 A1 | 6/2006 |
| EP | 1 430 835 A1 | 6/2004 |

(Continued)

OTHER PUBLICATIONS

Extended European Search Report issued Jul. 27, 2011, in European Patent Application No. 11155370.7.

(Continued)

*Primary Examiner* — Anastasia Midkiff
(74) *Attorney, Agent, or Firm* — Oblon, Spivak, McClelland, Maier & Neustadt, L.L.P.

(57) ABSTRACT

An X-ray image diagnosis apparatus includes: an imaging unit supporting an X-ray generation unit and an X-ray detection unit to face each other to take an image of a subject placed on a bed top panel; a control unit to execute a step movement process of at least one of the imaging unit and top panel and take images of the subject at plural stages; and an image processing unit that processes image data taken at the plural stages. The control unit sets plural regions of interest (ROI) in an imaging area of the subject when an image is taken after a contrast medium is injected into the subject, measures a change of an image level in the ROI to detect a flow of the contrast medium, and makes at least one of the imaging unit and top panel move to the next imaging stage based on the detection result.

3 Claims, 10 Drawing Sheets

(56) References Cited

U.S. PATENT DOCUMENTS

| | | | |
|---|---|---|---|
| 5,917,883 A * | 6/1999 | Khutoryansky et al. | 378/116 |
| 6,052,476 A * | 4/2000 | Qian et al. | 382/130 |
| 6,195,450 B1 | 2/2001 | Qian et al. | |
| 7,406,148 B2 | 7/2008 | Russinger et al. | |
| 2002/0041654 A1* | 4/2002 | Hayashi | 378/196 |
| 2004/0127789 A1 | 7/2004 | Ogawa | |
| 2006/0140336 A1 | 6/2006 | Russinger et al. | |

FOREIGN PATENT DOCUMENTS

| | | |
|---|---|---|
| JP | 6-237924 | 8/1994 |
| JP | 11-318877 A | 11/1999 |
| JP | 2001-269333 A | 10/2001 |
| JP | 2002-095654 A | 4/2002 |
| JP | 2004-57506 A | 2/2004 |
| JP | 2007-167664 A | 7/2007 |

OTHER PUBLICATIONS

Office Action issued Dec. 3, 2013 in Japanese Patent Application No. 2010-037300 with partial English language translation.

Office Action issued Mar. 18, 2014 in Japanese Patent Application No. 2010-037300 filed Feb. 23, 2010 (with Partial English Translation).

* cited by examiner

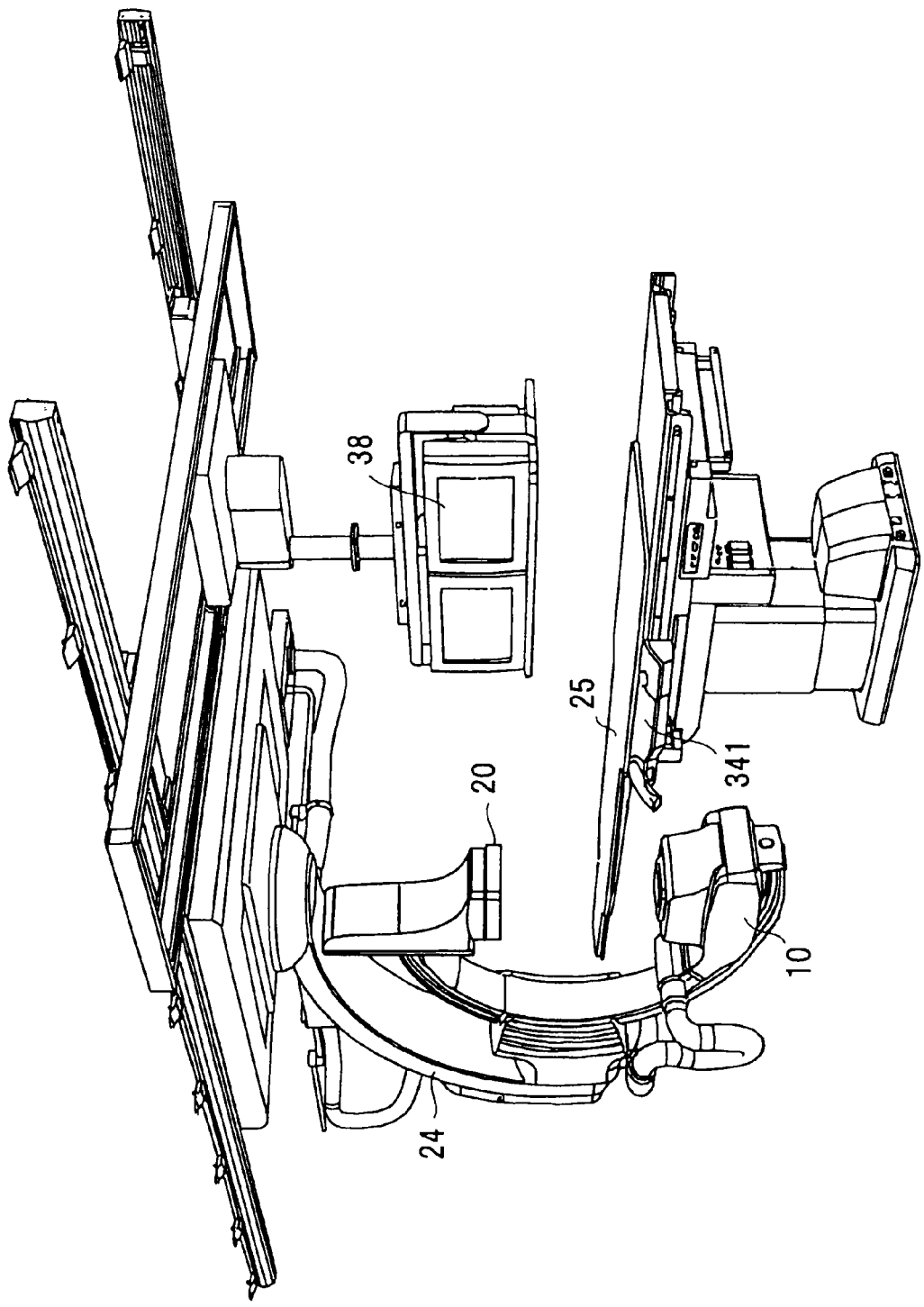

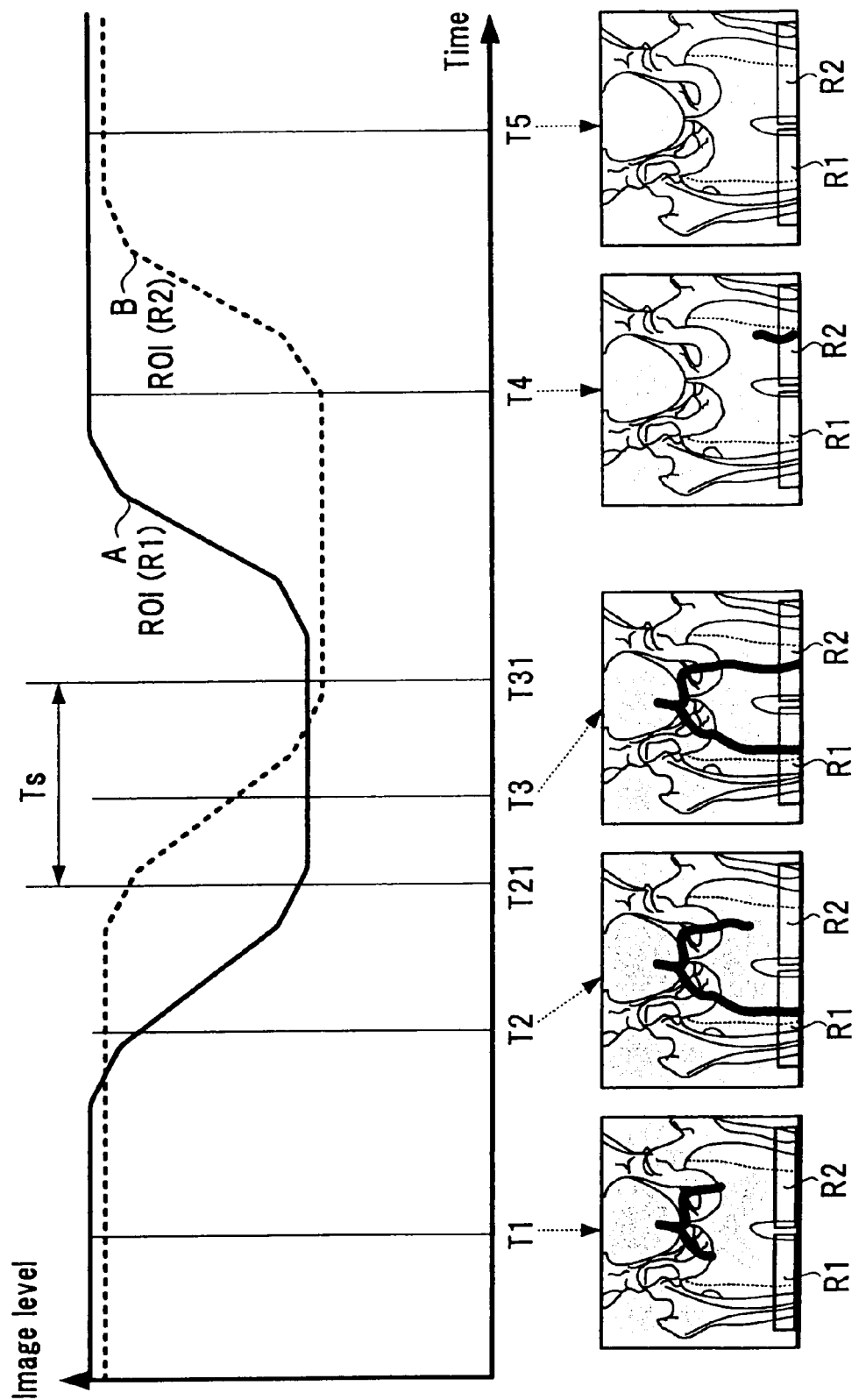

R0

R0

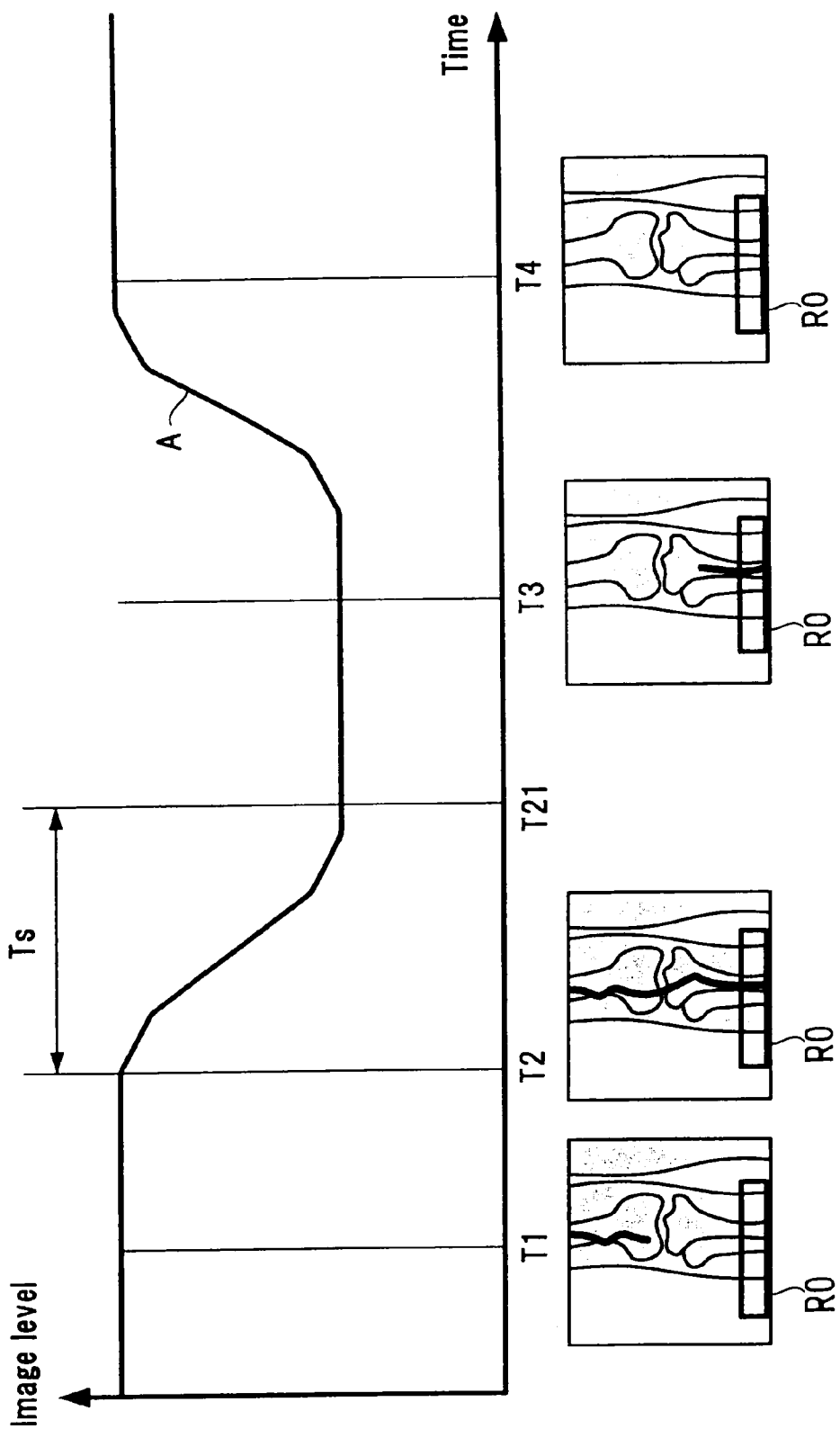

X-RAY IMAGE DIAGNOSIS APPARATUS AND X-RAY IMAGE PROCESSING METHOD

CROSS-REFERENCE TO RELATED APPLICATION

This application is based upon and claims the benefit of priority from the prior Japanese Patent Application No. 2010-037300, filed on Feb. 23, 2010, the entire contents of which are incorporated herein by reference.

FIELD

Embodiments described herein relate to an X-ray image diagnosis apparatus and an X-ray image processing method that are suitable for generating long image data.

BACKGROUND

In the examination of a circulatory organ, in order to look at the state of microscopic blood vessels, a contrast medium has been injected into the blood vessels in some cases to take an image. For example, the following method is known, a method of performing a subtraction process on a mask image, which is taken before the contrast medium is injected into the blood vessels, and a contrast image, which is taken with the injected contrast medium, to obtain a subtraction image in which an angiographic portion is enhanced and using the subtraction image as a diagnosis image.

When an image of lower limbs or the like is taken angiographically, the image is, in some cases, taken with stepping DSA (Digital Subtraction Angiography) as a top panel of a bed slides incrementally. However, in the process of making the top panel slide in accordance with the flow of the contrast medium, the timing of sliding could vary depending on how skillful an operator is and other factors. In particular, if the flows of the contrast medium are different in both legs due to the state of narrowed blood vessels, it is difficult to fix the timing to make the top panel slide. Therefore, an appropriate stepping DSA image may not be obtained.

JP-A-06-237924 discloses an X-ray diagnosis apparatus that is designed to move the bed in accordance with the movement of the contrast medium. In the above example, plenty of ROIs are set on an image. Whether the contrast medium flows in is determined based on a change in the average ROI density. The average velocity of the contrast medium passing through N regions is then calculated, and the movement of the bed is controlled based on a result of the calculation.

However, in the above example, the flow of the contrast medium in the patient does not match the slide timing of the bed in such cases as where the velocities of blood flows are different in both legs due to the state of narrowed blood vessels, it may take time to obtain an appropriate image.

BRIEF DESCRIPTION OF THE DRAWINGS

FIG. 2 is a perspective view showing the overall configuration of an X-ray image diagnosis apparatus according to the embodiment.

FIG. 7 is an explanatory diagram showing changes in an image level of a ROI as well as the timings of shifts to the subsequent stages.

FIG. 12 is an explanatory diagram showing an image level of a ROI as well as the timings of shifts to the subsequent stages when an image of one leg is taken.

DETAILED DESCRIPTION

An X-ray image diagnosis apparatus of an embodiment including:

an imaging unit that supports an X-ray generation unit which emits an X ray to which a subject is exposed, and an X-ray detection unit which detects the X-ray that has passed through the subject, in such a way that the X-ray generation unit and the X-ray detection unit face each other and is possible to take an image of the subject placed on a top panel of a bed;

a control unit that performs control in such a way that a step movement process of at least one of the imaging unit and top panel is carried out and images of the subject are taken at a plurality of stages; and an image processing unit that processes image data taken at a plurality of the stages, wherein the control unit sets a region of interest in an imaging area of the subject when an image is taken after a contrast medium is injected into the subject, measures a change of an image level in the region of interest to detect a flow of the contrast medium, and makes at least one of the imaging unit and top panel move to the next imaging stage on the basis of a result of the detection.

The following describes in detail an X-ray image diagnosis apparatus according to an embodiment with reference to the accompanying drawings. Incidentally, in each diagram, the same portions are indicated by the same reference symbols.

Figure 1:
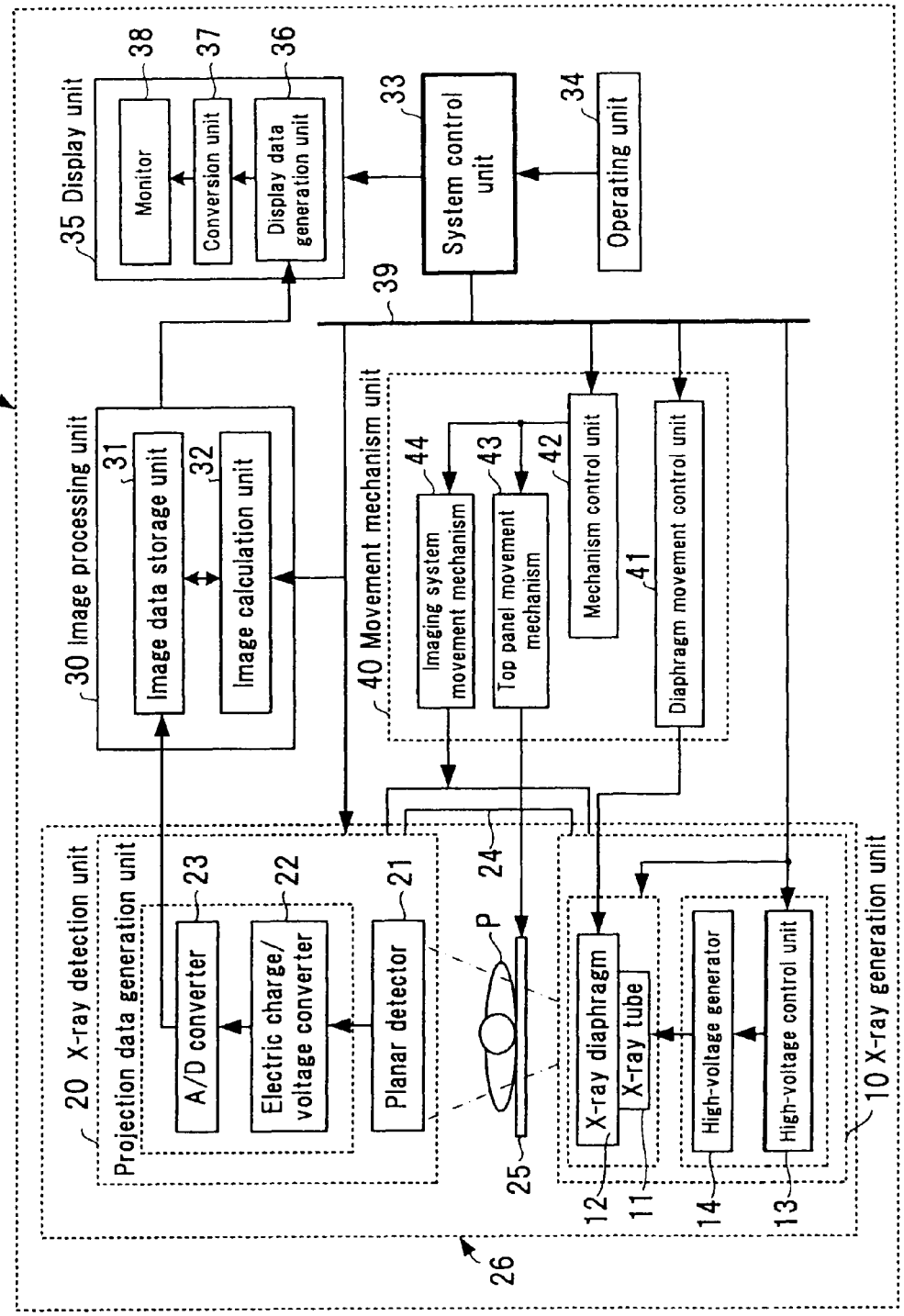
FIG. 1 is a block diagram showing the configuration of an X-ray image diagnosis apparatus according to an embodiment.

FIG. 1 is a block diagram showing the configuration of an X-ray image diagnosis apparatus (Angiography apparatus) according to an embodiment. In FIG. 1, an X-ray image diagnosis apparatus 100 includes an X-ray generation unit 10, which generates an X-ray for a subject P, and an X-ray detection unit 20, which detects, in a two-dimensional way, the X-ray that has passed through the subject P and generates X-ray projection data based on a result of the detection.

The X-ray generation unit 10 has an X-ray irradiation unit, which includes an X-ray tube 11 and an X-ray diaphragm 12, and a high-voltage generation unit which includes a high-voltage control unit 13 and a high-voltage generator 14. The X-ray tube 11 is a vacuum tube that produces X-ray electrons, the X-ray electrons emanating from a cathode (filament), wherein the electrons are then accelerated by high voltage and collide with a tungsten anode, thereby generating an X-ray.

The high-voltage control unit 13 controls the high-voltage generator 14 in accordance with an instruction signal from a system control unit 33 (described below), as well as X-ray irradiation conditions such as the tube current and voltage of the X-ray tube 11, the pulse width of the X-ray, irradiation cycles, imaging zones and irradiation time.

The X-ray detection unit 20 includes a planar detector 21, an electric charge/voltage converter 22 which converts an electric charge readout from the planar detector 21 into voltage, and an A/D converter 23 which converts an output of the electric charge/voltage converter 22 into a digital signal. The A/D converter 23 outputs X-ray projection data. The electric charge/voltage converter 22 and the A/D converter 23 make up a projection data generation unit.

The X-ray generation unit 10 and the X-ray detection unit 20 are supported by an arm (C arm) 24. The C arm 24 is able to move in a body-axis direction of the subject P placed on a top panel 25 of a bed and also able to rotate upon the body axis of the subject P. Incidentally, the X-ray generation unit 10 and the X-ray detection unit 20 constitute an imaging unit 26. As the C arm 24 rotates, the imaging unit 26 rotates around the subject P, making it possible to take images of the subject P in different angular directions.

The X-ray image diagnosis apparatus 100 also includes an image processing unit 30, a system control unit 33, an operating unit 34 and a display unit 35. The image processing unit 30 processes X-ray projection data supplied from the A/D converter 23 to generate and store image data. The image processing unit 30 has an image data storage unit 31 and an image calculation unit 32. In the image data storage unit 31, X-ray projection data are sequentially stored and image data are created. The image calculation unit 32 performs imaging and calculation processes on the generated image data when necessary for the following purposes, among other things, for example enhancing edges and improving S/N.

The image data generated by the image processing unit 30 is fed to the display unit 35, which then displays the image data. The display unit 35 displays the image data supplied from the image data storage unit 31. The display unit 35 includes a display data generation unit 36, a conversion unit 37 and a monitor 38. The display data generation unit 36 combines image data with incidental information and generates display data by converting the image data into a predetermined display format. The conversion unit 37 performs D/A (Digital/Analog) conversion and television format conversion on the display data to generate an image signal, which the monitor 38 such as a liquid crystal display, then displays.

The operating unit 34 is used by a doctor or other users to input various commands or execute other operations. The operating unit 34 includes an interactive interface that is equipped with input devices, such as a mouse, keyboard, trackball and joystick, a display panel, various switches, or the like. The operating unit 34 is also used to perform such operations as setting the travelling speed and direction of the top panel 25, the rotating/traveling direction and rotating/traveling speed of an imaging system, and X-ray irradiation conditions including the tube current and voltage.

The system control unit 33 includes a CPU and a storage circuit (not shown). The system control unit 33 overall controls each unit of the X-ray image diagnosis apparatus 100 through a bus line 39 on the basis of input, setting and selection information supplied from the operating unit 34.

The X-ray image diagnosis apparatus 100 also includes a movement mechanism unit 40. The movement mechanism unit 40 has a diaphragm movement control unit 41 and a mechanism control unit 42. The diaphragm movement control unit 41 controls the movement of diaphragm blades or the like in the X-ray diaphragm 12. The mechanism control unit 42 controls a movement mechanism 43 of the top panel 25 on which the subject P is placed as well as the movement of an imaging system movement mechanism 44. The movement mechanism unit 40 operates as the operating unit 34 is operated. The movement mechanism unit 40 controls the movement of each unit under the control of the system control unit 33.

FIG. 2 is a perspective view showing the overall configuration of an X-ray image diagnosis apparatus 100 (Angiography apparatus) according to an embodiment. In FIG. 2, the X-ray generation unit 10 and the X-ray detection unit 20 are supported by the C arm 24 so as to face each other. The bed is arranged relative to the C arm 24. On the top panel 25 of the bed a subject is placed, and it is possible for the mechanism control unit 42 to control the height and position of the top panel 25.

For example, the C arm 24 is attached to rails placed in a ceiling section and able to move in the body-axis direction, from the head (Cranial) of the subject to the leg (Caudal). Moreover, as the C arm 24 rotates, the imaging unit 26 (the X-ray generation unit 10 and the X-ray detection unit 20) rotates upon the body axis around the periphery of the subject. The imaging unit 26 slides and rotates along the C arm 24.

The X-ray projection data is processed by the image processing unit 30, the image data is displayed on the monitor 38. The monitor 38 is for example attached to the ceiling section. An operating unit 341 is attached to the bed. As the operating unit 341 is operated, the system control unit 33 performs such processes as controlling the height of the top panel 25 and the movement and rotation of the C arm 24, adjusting an X-ray irradiation range, and controlling irradiation timing.

The following describes a method of generating image data using the image processing unit 30. One example of the test that uses the X-ray diagnosis apparatus 100 is the examination of a lower-limb region, an image of a broad range from the abdomen to the toes, may be taken. There is no X-ray detector whose visual field enables an image of a broad range, such as lower limbs, to be taken at one time. Therefore, images are taken several times to cover the whole range.

In the test on the lower-limb region, the step movement of the imaging unit 26 (the X-ray generation unit 10 and the X-ray detection unit 20) is sequentially carried out from an initial imaging location, images are each taken at a plurality of stages. That is, in the stepping DSA imaging process, the top panel 25 moves in the direction of the blood flow of the subject P (or in the body-axis direction when the lower-limb region is examined) and moves to a predetermined imaging area earlier than the contrast medium arrives. Then, the top panel 25 stops moving temporarily at an imaging location and waits until the contrast medium, which is injected into the blood vessels of the lower limbs arrives. When the contrast medium has arrived, an image is then taken. After the image is taken, the top panel 25 quickly moves to the next imaging location (stage). Such a method is repeatedly carried out to collect DA image data at a plurality of imaging locations.

Therefore, it is possible to obtain a plurality of image data items from the abdomen to the toes. A plurality of the generated DA image items is put together in the body-axis direction to generate long image data. Therefore, it is possible to observe the blood vessels in the broad lower-limb region on one X-ray image.

FIG. 3A to FIG. 3D are diagrams explaining how to take an image of the lower-limb region of the subject P with the use of the X-ray diagnosis apparatus 100 according to the embodiment. FIG. 3A to FIG. 3D schematically show a movement operation of the imaging unit 26 relative to the top panel 25, as well as an example of a taken image thereof.

Figure 3A:
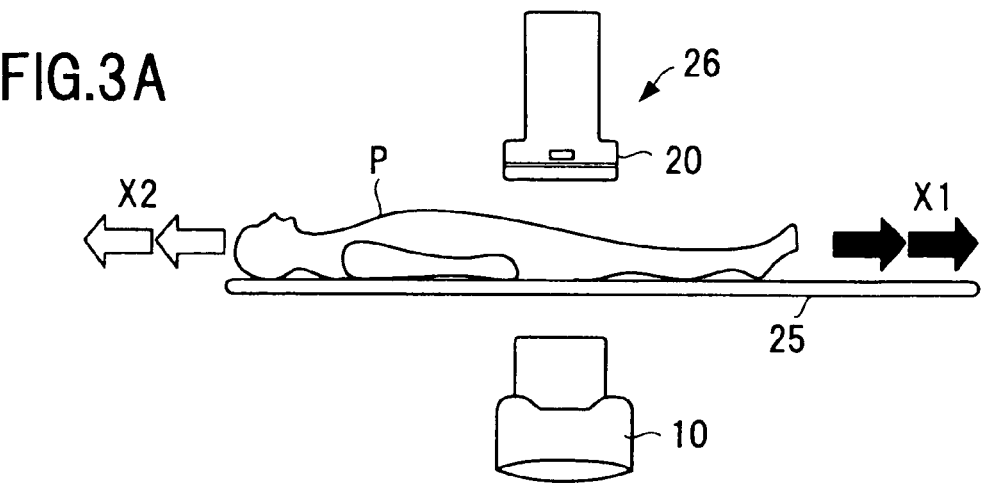
FIG. 3A to FIG. 3D are explanatory diagrams showing an operation of collecting mask images and contrast images.

As shown in FIG. 3A, the X-ray generation unit 10 and X-ray detection unit 20 of the imaging unit 26 are connected together through the C arm 24, the X-ray detection unit 20 is installed so as to face the X-ray generation unit 10. Between the X-ray generation unit 10 and the X-ray detection unit 20, the subject P placed on the top panel 25 is positioned. The top panel 25 is able to move in the body-axis direction while carrying the subject P. Accordingly, the step movement of the top panel 25 takes place relative to the imaging unit 26, and it is possible to obtain image data at a plurality of stages.

Incidentally, when the subject P is observed with the use of the X-ray, there are the following modes, a fluoroscopic mode in which image data is obtained with a low dose of X-rays emanating from the X-ray tube 11, and an imaging mode in which image data (diagnosis information) is acquired with a high dose of X-rays emanating from the X-ray tube 11.

When mask images are collected, the images are taken as the top panel 25 moves incrementally in a direction indicated by arrow X1 in FIG. 3A. The mask images are collected before the contrast medium is injected. For example, the images are taken from the toes of the subject P to the abdomen with a plurality of steps.

Figure 3B:
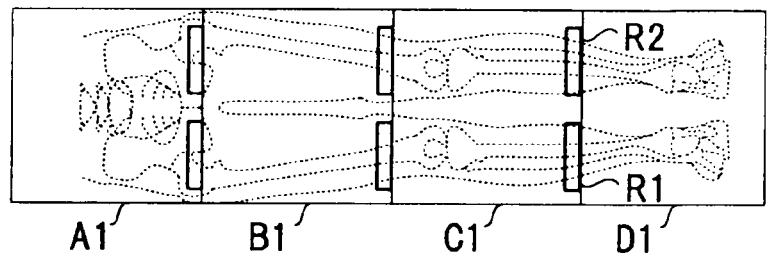

FIG. 3B shows a plurality of mask images (A1, B1, C1 and D1) which are sequentially taken by stepping imaging from the toes to the abdomen. A plurality of the mask images is arranged so as to overlap with each other at the front and rear parts in the traveling direction, there are no omissions in the taken images. Incidentally, in the case of FIG. 3B, for each of the images A1 to D1, ROIs (regions of interest: R1 and R2) are set. For example, ROIs (R1 and R2) may be set at a location where a current-step imaging area and a next-step imaging area overlap or in the vicinity thereof.

Figure 3C:
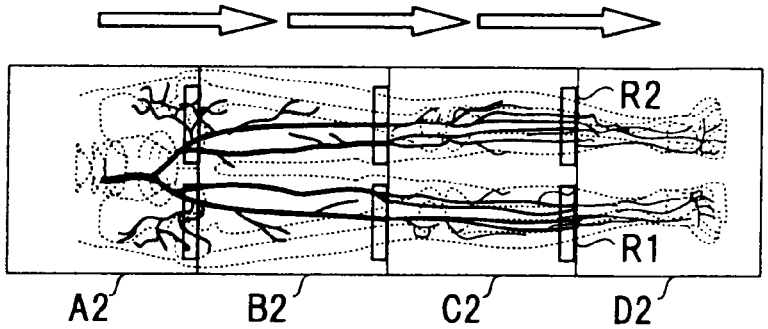

FIG. 3C shows an operation of collecting contrast images after the contrast medium is injected. In order to collect contrast images, for example the top panel 25 moves in the direction of the arrow X2 shown in FIG. 3A and the images are taken from the abdomen of the subject P to the toes with a plurality of steps. FIG. 3C shows a plurality of contrast images (A2, B2, C2 and D2) which are sequentially taken by stepping imaging from the abdomen to the toes. In FIG. 3C, contrast-medium images (blood-vessel images) are indicated by bold lines.

Figure 3D:
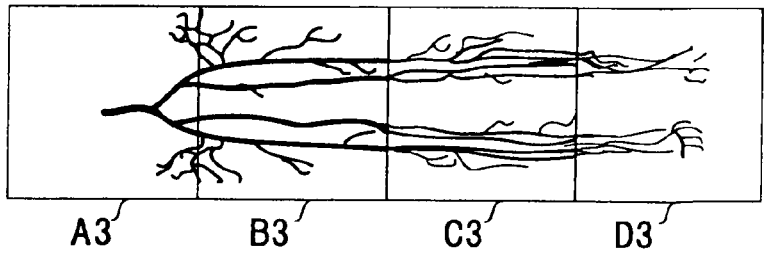

FIG. 3D shows one example of subtraction images. The subtraction images are generated by performing a subtraction process on the mask image data and the contrast image data, possible to obtain the subtraction images (A3, B3, C3 and D3) in which angiographic portions are enhanced.

According to the embodiment, for each of both legs, the region of interest (ROI) is set, when the mask images are collected, the pixel values (image levels) of the ROIs are measured. Moreover, when the contrast images are collected, the pixel values (image levels) of the ROIs are measured. On the basis of changes in the image levels, the influx of the contrast medium is detected. On the basis of the detection result, the top panel 25 automatically slides to the next stage.

For each of both legs, the ROI is set. Therefore, it is possible to make the top panel 25 slide automatically to the next stage in accordance with the timing of the leg in which the pixel values change more slowly (the leg in which the contrast medium flows more slowly). Moreover, the ROI is set in a lower portion of a screen and is set at a portion where the current-step imaging area and the next-step imaging area overlap. Therefore, it is possible to obtain a stepping DSA image suitable for diagnosis.

Figure 4:
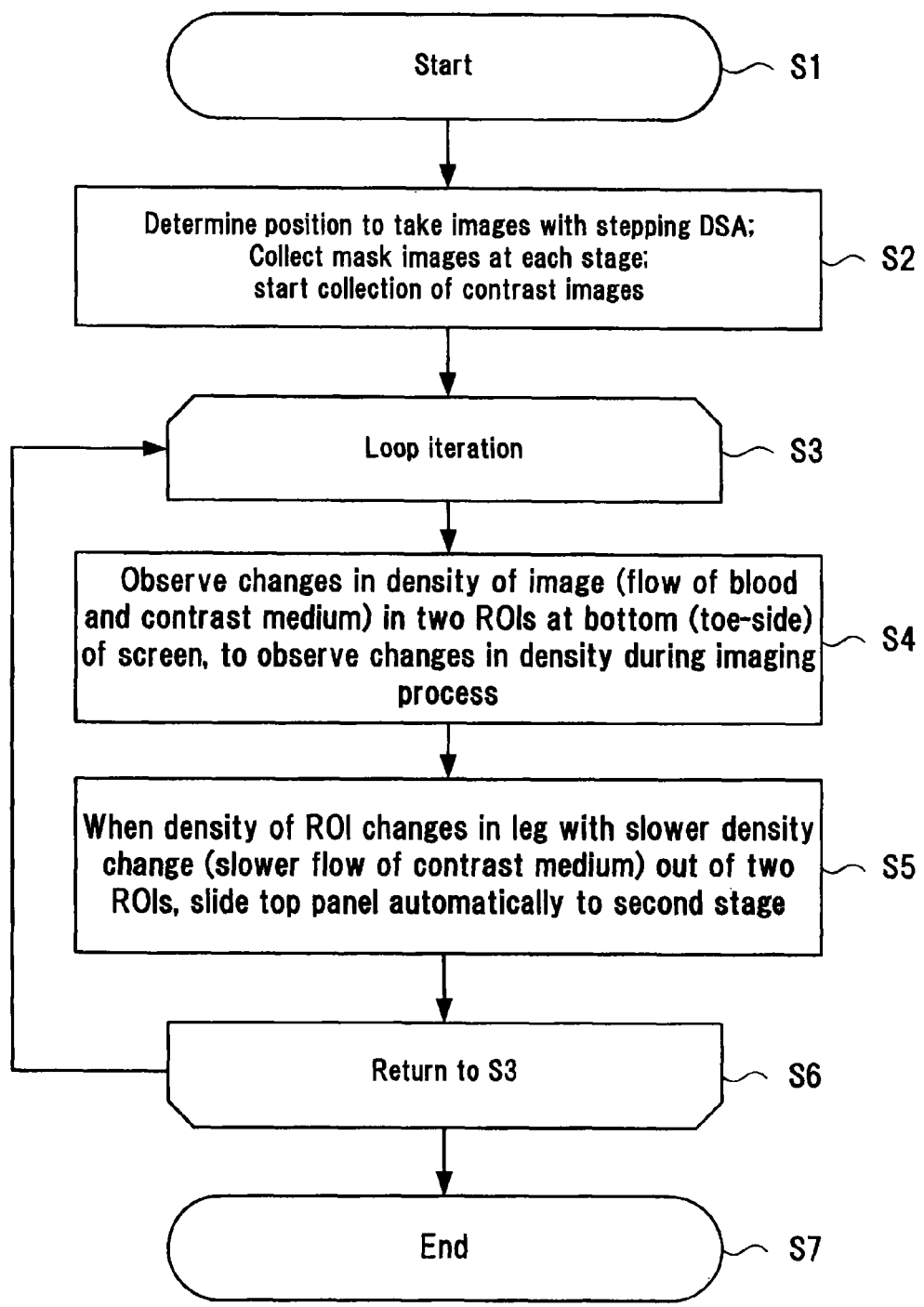
FIG. 4 is a flowchart showing an operation of collecting mask images and contrast images.

FIG. 4 is a flowchart showing an operation of collecting mask images and contrast images according to the embodiment. FIG. 5A to FIG. 5D and FIG. 6A to FIG. 6C are explanatory diagrams explaining the flows of the contrast medium at first and second stages.

In FIG. 4, step S1 is a start step. At the next step S2, a position is determined to take images with stepping DSA, the images of the lower limbs are taken at a plurality of stages (four stages, for example) to collect the mask images. When the mask images are taken, the ROIs are set in the image that is taken at each stage. Incidentally, any methods are available in determining the number of steps for the stepping DSA imaging process.

After the mask images are taken, the processes of steps S3 to S6 are repeatedly performed, therefore, the contrast images are automatically collected at each of the stages (from the first to fourth stages). That is, at step S4, changes in the density of the images (the flow of blood and contrast medium) are observed in the ROIs (R1 and R2), which are set at two locations at the bottom (the toe-direction side) of the screen, while the contrast images are being taken.

Figure 5A:
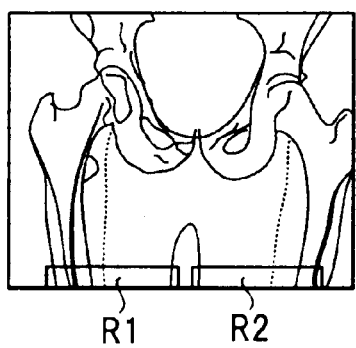
FIG. 5A to FIG. 5D are explanatory diagrams showing flows of a contrast medium at a first stage.
Figure 5B:
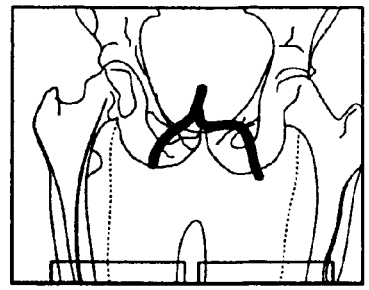
Figure 5C:
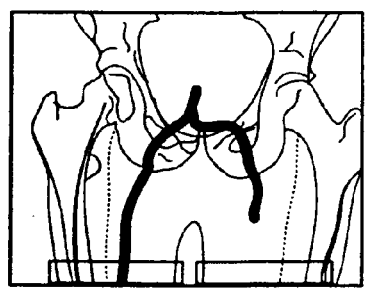
Figure 5D:
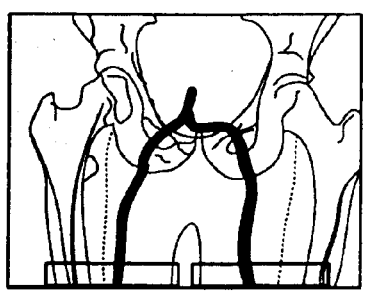

FIG. 5A shows a taken image of the contrast image at the first stage. FIG. 5A shows an example in which the ROIs (R1 and R2) are set at two locations (one for the left leg and the other for the right leg) at the bottom of the screen. FIG. 5B shows the contrast medium (indicated by bold lines) that has started flowing. FIG. 5C shows the contrast medium that has reached one ROI (R1) earlier than the other. FIG. 5D shows the contrast medium that has reached both ROIs (RI and R2). For example, when the blood vessels in the left leg are clogged, the flow of the contrast medium in the left leg is slow, meaning that the contrast medium's arrival at the ROI (R2) is delayed.

The system control unit 33 measures the image levels in the ROIs (R1 and R2). That is, for the legs to be examined, the system control unit 33 observes the image levels (pixel values) in each of the legs. The influx of the contrast medium into the ROIs (R1 and R2) results in a change in the density of the image. Therefore, based on the changes of the image levels, it is possible to detect the flow of the contrast medium.

Moreover, at step S5, among the two ROIs (R1 and R2), on the basis of the changing timing of the ROI (R2) in which the density of the image changes more slowly, the mechanism control unit 42 issues a slide instruction to the top panel movement mechanism 43 so that the top panel 25 is so controlled as to move to the next stage.

As for the timing of the movement to the next stage, for example, after a predetermined period of time Ts has passed since a change in the average value of the image levels of the ROI (R2), the top panel 25 starts to slide. For example, the time Ts is so set as to be the time needed for a changing condition in the ROI (R2) to become saturated after a change in the density of the image or other times. Alternatively, the time Ts may be so set as to be the time needed for the changing condition to be stabilized right after the time when the density of the image starts changing.

As shown in FIGS. 5C and 5D, if there is a difference in the velocity of blood flow between both legs due to the state of narrowed blood vessels, the blood vessels with slower blood flow are regarded as being seriously narrowed. Accordingly, the images are taken in accordance with the flow of the contrast medium in the leg with slower blood flow. Then, the process automatically moves to the next stage so that the contrast images are taken in a timely manner.

Then, the process returns to step S3 from step S6, and similar processes are repeated to collect the contrast images at the next stage (the second stage, for example).

Figure 6A:
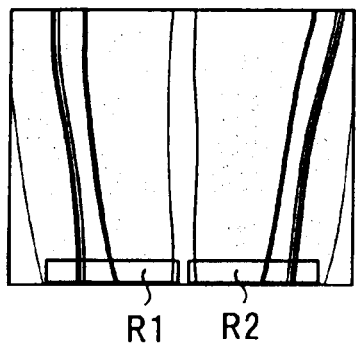
FIG. 6A to FIG. 6C are explanatory diagrams showing flows of a contrast medium at a second stage.
Figure 6B:
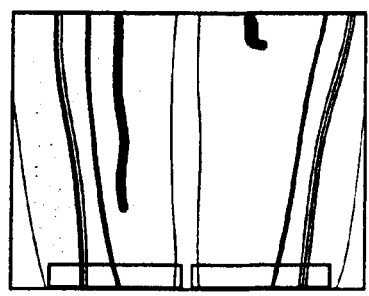
Figure 6C:
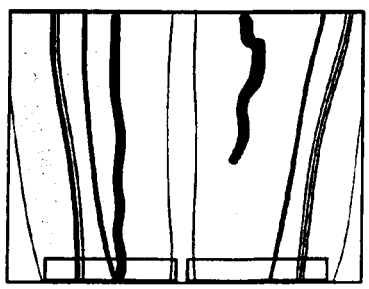

FIG. 6A shows a taken image of the contrast image at the second stage. In the case of FIG. 6A, the ROIs (R1 and R2) are set at two locations (one for the left leg and the other for the right leg) at the bottom of the screen. FIG. 6B shows the flow of the contrast medium at the second stage. FIG. 6C shows the contrast medium that has reached the ROI (R1) earlier than the other. When the blood vessels in the left leg are clogged, the flow of the contrast medium in the left leg is slow, meaning that the contrast medium's arrival at the ROI (R2) is delayed.

The images are taken in accordance with the flow of the contrast medium in the leg with slower blood flow. In addition, the process automatically moves to the next stage so that the contrast images are collected in a timely manner. After the images are taken at all the stages, the process proceeds to step S7 and ends.

FIG. 7 is an explanatory diagram showing changes in the image level (density) of the ROIs (R1 and R2) as well as the timings of shifts to the subsequent stages. In FIG. 7, the vertical axis represents the image levels of the ROIs (R1 and R2), the horizontal axis represents time. Solid line A represents a change characteristic of the image level of the ROI (R1). Dotted line B represents a change characteristic of the image level of the ROI (R2). The transition of the contrast-medium image at the first stage from timing T1 to T5 is shown on the horizontal axis.

For example, if the timing at which the image level of the ROI (R2) has changed is T21, the process steps to the next stage after a predetermined period of time (Ts) has passed since the timing T21. The time Ts may be so set as to be the time (T31) needed for a changing condition in the ROI (R2) to become saturated after a change in the density of the image or the time needed for the changing condition to be stabilized right after the time (T21) when the density of the image starts changing.

Incidentally, at time T4, the contrast medium has already passed through the ROI (R1), the image level has risen. Meanwhile, the contrast medium is still passing in the ROI (R2), therefore, the image level is low. At time T5, the contrast medium has passed even through the ROI (R2), the image level has gone up.

Figure 8A:
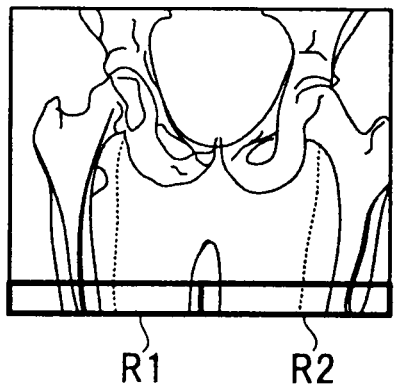
FIG. 8A to FIG. 8E are explanatory diagrams showing variant examples of the shape of ROIs.
Figure 8B:
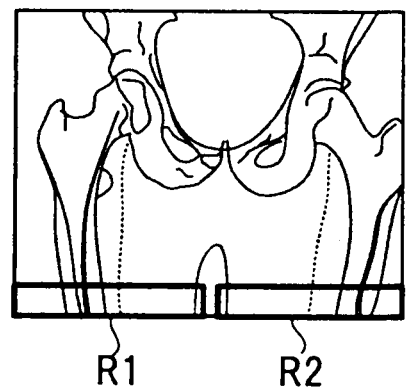
Figure 8C:
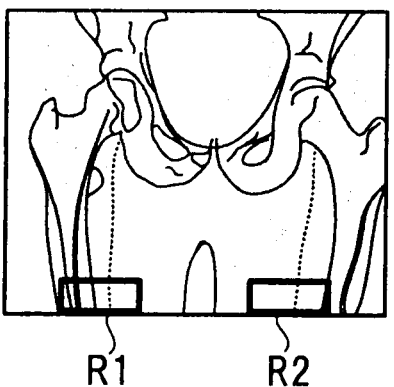
Figure 8D:
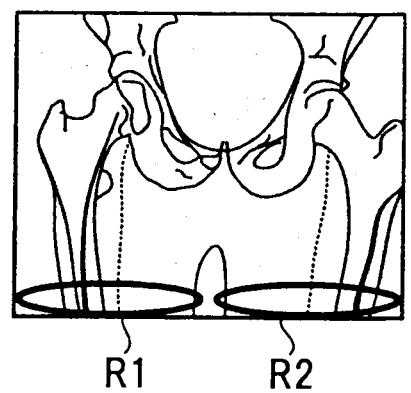

FIG. 8A to FIG. 8D are explanatory diagrams showing variant examples of the shape of the ROIs (R1 and R2). As shown in FIG. 8A, the ROIs (R1 and R2) may be rectangles, which are made by dividing the lower portion of the screen into two. As shown in FIG. 8B, the ROIs (R1 and R2) may be rectangles with a space at a central portion, which are made by dividing the lower portion of the screen into two. As shown in FIG. 8C, the ROIs (R1 and R2) may be in the shape of a rectangle, with one positioned at a central portion of the left leg and the other at a central portion of the right leg. As shown in FIG. 8D, the ROIs (R1 and R2) may be ellipses.

Figure 8E:
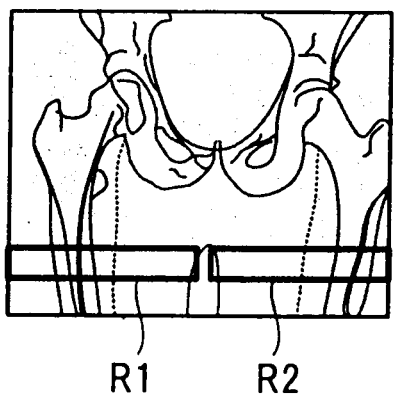

Incidentally, the ROIs (R1 and R2) are not necessarily set in a bottom portion of the screen. For example, as shown in FIG. 8E, the ROIs (R1 and R2) may be set at locations slightly higher than the bottom portion. In the example shown in FIG. 8E, the time needed for the contrast medium to reach the bottom portion is taken into consideration relative to the timing at which the image level of the ROI (R1 or R2) has changed, the process steps to the next stage after a predetermined period of time has passed.

According to the embodiment, the images of the to-be examined blood vessels can be taken seamlessly across the steps, and it is possible to prevent the images from being taken again, which is useful in reducing the examination time, the radiation exposure and the amount of the contrast medium.

The following describes an X-ray image diagnosis apparatus according to a second embodiment.

The example described above is an example in which the images of the lower limbs and both legs are taken. However, the second embodiment is about setting the ROI when images of only one leg are taken with stepping DSA, as well as setting the timings of shifts to the subsequent stages. When images of one leg are taken, the number of ROIs is reduced from two to one. The following provides a specific description.

Figure 9A:
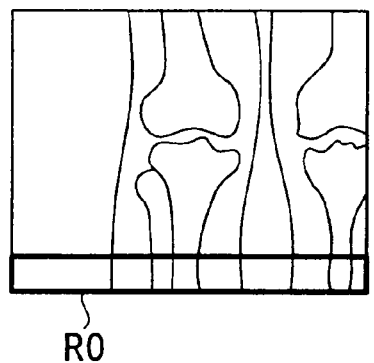
FIG. 9A and FIG. 9B are explanatory diagrams showing images and ROIs when an image of one leg is taken in an X-ray image diagnosis apparatus of a second embodiment as well as when an image of both legs is taken.
Figure 9B:
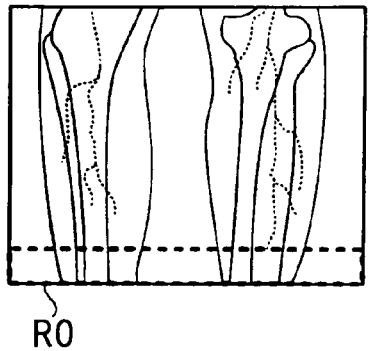

Before the stepping DSA imaging process, the positions of the legs are adjusted so that one leg appears in the left section of the image and the other in the right section if the images of both legs are taken. If the images of one leg are taken, the position of the leg is adjusted so that the leg appears at the center of the image. FIG. 9A shows an image of one leg that is taken, and FIG. 9B shows an image of both legs that is taken.

FIG. 9A shows an example of the image of one leg, that is taken as well as of a ROI (R0). FIG. 9B shows an example of the image of both legs, that is taken as well as of a ROI (R0) so that a comparison is made. When the image of one leg is taken, an X-ray image whose central portion is dark because the image of the leg is created in a central portion of the image. When the image of both legs is taken, an X-ray image whose central portion is bright but both sides (the portions in which the left and right legs exist) dark because X-rays pass through without any obstacles between both legs.

Figure 10:
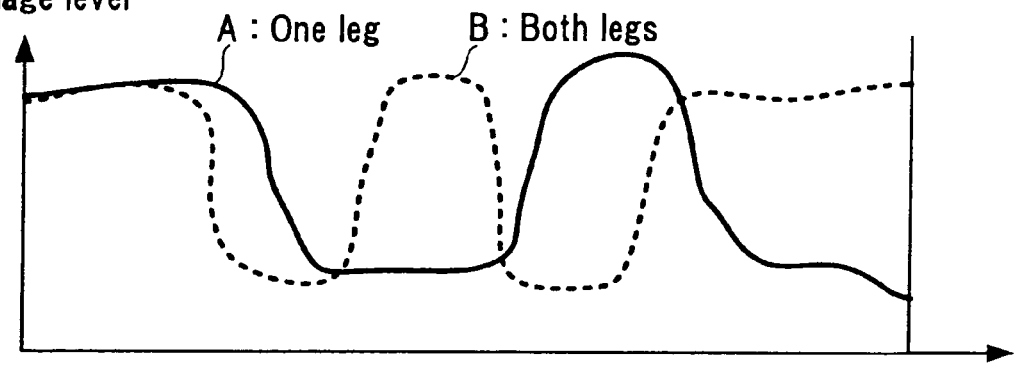
FIG. 10 is a characteristic chart showing profiles in a ROI when an image of one leg is taken as well as when an image of both legs is taken.

FIG. 10 shows a profile of the X-ray image of one leg that is taken in the ROI (R0), as well as that of the X-ray image of both legs that is taken in the ROI (R0). The ROI (R0) covers the entire region at the bottom of the screen. Solid line A represents the profile of the image of one leg that is taken. Dotted line B represents the profile of the image of both legs that is taken. The vertical axis represents the image level. The image level is low in a portion where a leg exists.

Therefore, at the start of the imaging process, a determination is made as to a characteristic of the profile of the X-ray image to recognize whether the image of one leg or both legs is taken. When the image of one leg is taken, one ROI is set. Alternatively, a one-leg imaging mode may be input by manual operation to set one ROI.

When images are taken with stepping DSA, an imaging program for one-leg stepping DSA and an imaging program for both-leg stepping DSA are provided. The system control unit 33 links a result of profile determination (or information input by user operation) to an imaging program and selects the imaging program.

Figure 11A:
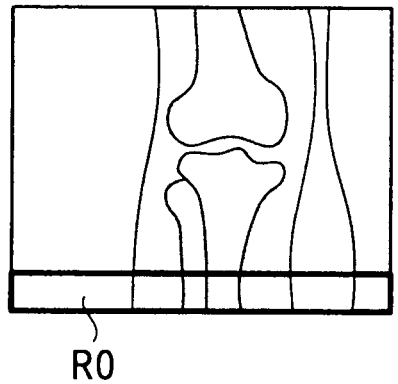
FIG. 11A to FIG. 11E are explanatory diagrams showing variant examples of the shape of a ROI when an image of one leg is taken.
Figure 11B:
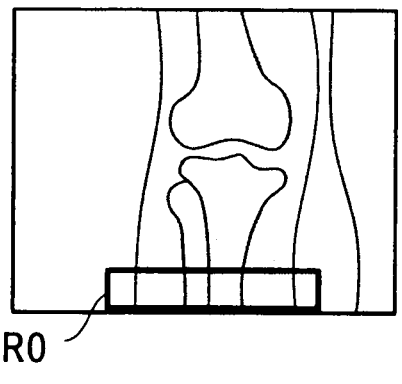
Figure 11C:
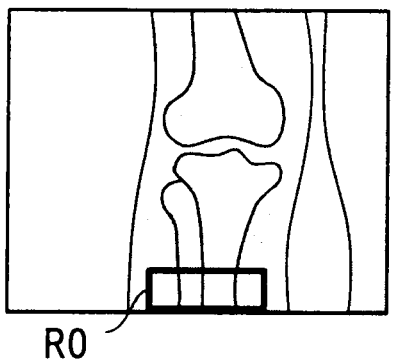
Figure 11D:
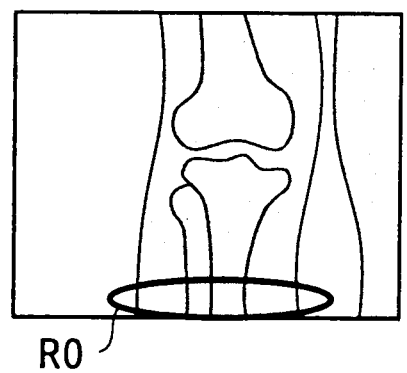
Figure 11E:
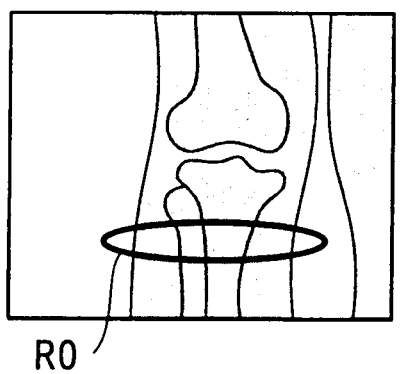

FIG. 11A to FIG. 11E are explanatory diagrams showing one example of the shape of the ROI (R0) when the image of one leg is taken. As shown in FIG. 11A, the ROI (R0) may be a rectangle covering the entire bottom portion of the screen. As shown in FIG. 11B, the ROI (R0) may be a rectangle covering a leg area at the bottom of the screen. As shown in FIG. 11C, the ROI (R0) may be in the shape of a rectangle, covering a blood-vessel area of the leg. As shown in FIG. 11D, the ROI (R0) may be an ellipse. Incidentally, the ROI (R0) is not necessarily set in a bottom portion of the screen. For example, as shown in FIG. 11E, the ROI (R0) may be set at location slightly higher than the bottom portion.

FIG. 12 is an explanatory diagram showing changes in the image level (density) of the ROI (R0) when the image of one leg is taken, as well as the timings of shifts to the subsequent stages. In FIG. 12, the vertical axis represents the image level of the ROI (R0), the horizontal axis represents time. Solid line A represents a change characteristic of the image level of the ROI (R0). The transition of the contrast-medium image at the first stage from timing T1 to T4 is shown on the horizontal axis.

For example, shown at time T1 is the situation where the contrast medium starts flowing in one leg (the right leg in the present example). Suppose that T2 is the time when the contrast medium has reached the ROI (R0) and the average value of the image level has changed. At timing T21, which comes after a predetermined period of time (Ts) has passed since timing T2, the process steps to the next stage. The time Ts may be so set as to be the time needed for a changing condition in the ROI (R0) to become saturated after a change in the density of the image or the time needed for the changing condition to be stabilized right after the time (T2) when the density of the image starts changing.

Incidentally, at time T3, the contrast medium has already passed in the ROI (R0), the image level is low. At time T4, which comes after the contrast medium has passed through the ROI (R0), the image level has risen. When the image of one leg is taken, the position and shape of the ROI is different from when the image of both legs is taken, as one ROI (R0) changes, the process moves automatically to the next step.

Incidentally, described as an example in the first embodiment is as follows, when the image of both legs is taken with stepping DSA, two ROIs are placed, a change in the image level of the ROI in which the contrast medium flows more slowly is checked, and the process automatically moves to the next stage. However, as for the ROIs, before the stepping DSA imaging process is performed, the decision as to which ROI is to be used may be made based on information manually input by user operation. That is, the positions and the number of the ROIs are determined after the decision as to which leg's blood-vessel image is to be observed or whether both legs' blood-vessel image is to be observed is made, the stepping DSA imaging process is then performed.

The selection of the ROI by user operation is carried out with information input from the operating unit 34. When one leg is measured, the system control unit 33 performs a step movement process as shown in FIG. 12 in accordance with the one-leg stepping DSA imaging program. In general, the leg in which the contrast medium flows more slowly is considered to have more narrowed blood vessels. However, in some cases, the leg that is actually to be treated has the faster flow of the contrast medium. Even in such a case, it is possible to automatically slide to the next stage and obtain an intended image.

According to the above-described embodiments, it is possible to acquire the stepping DSA images suitable for diagnosis, as well as to perform the stepping DSA imaging process in a timely manner regardless of how skillful an operator is.

Incidentally, the above has described an example in which the step movement processes of the imaging unit 26 are sequentially performed to take the images of the lower-limb region. However, not only is the lower-limb region examined, images of a broad area, such as the main artery stretching from the heart through the abdomen to the lower-limb region, can also be taken in the stepping DSA imaging process.

When the images of the subject are taken, all that is required is to move at least one of the imaging unit 26 and top panel 25 in the direction of the blood flow in a to-be-examined area. For example, when the images of the lower-limb region are taken, the blood flows in the body-axis direction of the subject. Therefore, the images are taken as at least one of the imaging unit 26 and top panel 25 moves in the body-axis direction. When the images of an arm are taken, the images are taken as the imaging unit 26 moves in the direction of the blood flow. Even when a detector for a small imaging area is used and the stepping movement process is gradually performed to take images within a narrow imaging region, the imaging unit 26 moves in the direction of the blood flow while the images are taken.

In the above-described embodiments is the planar detector 21 that is used for the X-ray detection unit 20. However, it is also possible to use an X-ray detection unit including an X-ray I.I. (Image Intensifier) and an X-ray television camera instead of the planar detector 21. According to an imaging method in which the X-ray I.I. is used, image information, which is obtained after an X ray has passed through the subject, is converted into an optical image in the X-ray I.I. Moreover, the optical image is taken by the X-ray television camera before being converted into electric signals. The X-ray image information, which has been converted into the electric signals, is then displayed on a monitor of the display unit after A/D conversion is performed.

Also described is an example in which the top panel 25 moves when the DA image data are collected in the stepping imaging process. However, with the top panel 25 fixed, the imaging unit 26 may move in the body-axis direction of the subject to track the contrast medium and to take images. That is, all that is required is to move at least one of the top panel 25 and imaging unit 26.

While certain embodiments have been described, these embodiments have been presented by way of example only, and are not intended to limit the scope of the inventions. Indeed, the novel apparatus and methods described herein may be embodied in a variety of the other forms; furthermore, various omissions, substitutions and changes in the form of the apparatus and methods described herein may be made without departing from the sprit of the inventions. The accompanying claims and their equivalents are intended to cover such forms or modifications as would fall within the scope and spirit of the inventions.

What is claimed is:

1. An X-ray image processing method, comprising:
   providing an imaging unit that supports an X-ray generation unit, which emits an X ray to which a subject is exposed, and an X-ray detection unit, which detects the X-ray that has passed through the subject, such that the X-ray generation unit and the X-ray detection unit face each other and such that it is possible to take an image of the subject placed on a top panel of a bed;
   performing control such that a step movement process of at least one of the imaging unit and the top panel is carried out and images of the subject are taken at a plurality of stages;
   setting a plurality of regions of interest for a plurality of locations in both legs of the subject when an image is taken after a contrast medium is injected into a lower limb of the subject;
   measuring a change of an image level in the regions of interest to detect a flow of the contrast medium and making at least one of the imaging unit and the top panel move to the next imaging stage on the basis of a change in the image level of a leg in which the contrast medium flows more slowly; and
   processing image data taken at the plurality of stages.

2. The method of claim 1, wherein
   at least one of the imaging unit and top panel is moved in the direction of a blood flow in a to-be examined area when an image of the subject is taken.

3. The method of claim 1, wherein:
   a determination is made, on the basis of a profile of an X-ray image or of information input by a user, as to whether an image of one or both legs is to be taken when an image is taken after the contrast medium is injected into a lower limb of the subject; and a plurality of regions of interest are set in a body-axis direction of the lower limb in response to a result of the determination to take an image of one or both legs.

* * * * *